(12) United States Patent
Wu et al.

(10) Patent No.: US 11,358,004 B2
(45) Date of Patent: Jun. 14, 2022

(54) SYSTEMS AND METHODS FOR RADIATION TREATMENT PLANNING BASED ON A MODEL OF PLANNING STRATEGIES KNOWLEDGE INCLUDING TREATMENT PLANNING STATES AND ACTIONS

(71) Applicants: DUKE UNIVERSITY, Durham, NC (US); The University of North Carolina at Charlotte, Charlotte, NC (US)

(72) Inventors: Qingrong Wu, Durham, NC (US); Yaorong Ge, Durham, NC (US); FangFang Yin, Durham, NC (US); Chunhao Wang, Durham, NC (US); Jiahan Zhang, Durham, NC (US); Manisha Palta, Durham, NC (US); Yang Sheng, Durham, NC (US)

(73) Assignees: Duke University, Durham, NC (US); The University of North Carolina at Charlotte, Charlotte, NC (US)

( * ) Notice: Subject to any disclaimer, the term of this patent is extended or adjusted under 35 U.S.C. 154(b) by 240 days.

(21) Appl. No.: 16/871,084

(22) Filed: May 11, 2020

(65) Prior Publication Data

US 2020/0353286 A1    Nov. 12, 2020

Related U.S. Application Data

(60) Provisional application No. 62/845,942, filed on May 10, 2019.

(51) Int. Cl.
*A61N 5/10* (2006.01)
*G16H 20/40* (2018.01)
*G16H 40/63* (2018.01)

(52) U.S. Cl.
CPC ......... *A61N 5/1031* (2013.01); *A61N 5/1038* (2013.01); *A61N 5/1039* (2013.01);
(Continued)

(58) Field of Classification Search
CPC ...... A61N 5/10; A61N 5/1031; A61N 5/1038; A61N 5/1039; A61N 5/103;
(Continued)

(56) References Cited

U.S. PATENT DOCUMENTS

2019/0333623 A1\* 10/2019 Hibbard ................. G16H 20/40
2021/0031054 A1\*  2/2021 Ranganathan ......... G16H 20/40

OTHER PUBLICATIONS

Li, X, et al. Automatic IMRT Planning Via Static Field Fluence Prediction (AIP-SFFP): A Deep Learning Method of Real-Time Prostate Treatment Planning. AAPM 61st Annual Meeting & Exhibition—Meeting Program—Abstract Information (/meetings/2019AM/programinfo/programAndx.php?pid=146706). 2 pages (2019).
(Continued)

*Primary Examiner* — Jurie Yun
(74) *Attorney, Agent, or Firm* — Olive Law Group, PLLC

(57) ABSTRACT

Systems and methods for radiation treatment planning based on a model of planning strategies knowledge including treatment states and treatment actions are disclosed. According to an aspect, a method includes receiving geometric characterization data of a target volume for radiation treatment of a patient. The method also includes receiving geometric characterization data of at least one organ at risk proximate the target volume. Further, the method includes constructing a model for applying a predetermined radiation dosage to the target volume based on the received data. The model includes treatment states and associated treatment actions selectable to implement at each state. The method includes presenting information about at least one treatment state, the treatment actions associated with the at least one treatment state, and the rewards associated with the treat-
(Continued)

ment actions associated with the at least one treatment state. The method also includes reconstructing the model.

27 Claims, 9 Drawing Sheets

(52) U.S. Cl.
CPC ............. *G16H 20/40* (2018.01); *G16H 40/63* (2018.01); *A61N 2005/1041* (2013.01)

(58) Field of Classification Search
CPC ........... A61N 2005/1041; G16H 20/40; G16H 40/63; G16H 50/50
See application file for complete search history.

(56) References Cited

OTHER PUBLICATIONS

Wang, W., et al. Atlas-Guided Fluence Initialization and Optimization for Pancreas SBRT: A Feasibility Study. APM 61st Annual Meeting & Exhibition—Meeting Program—Abstract Information (/meetings/2019AM/programinfo/programAndx.php?pid=146966). 2 pages (2019).

Zhang, J., et al. Artificial Intelligence-Driven Pancreas Stereotactic Body Radiation Therapy (SBRT) Treatment Planning. 61st Annual Meeting & Exhibition—Meeting Program—Abstract Information (/meetings/2019AM/programinfo/programAndx.php?pid=146714). 2 pages (2019).

* cited by examiner

SYSTEMS AND METHODS FOR RADIATION TREATMENT PLANNING BASED ON A MODEL OF PLANNING STRATEGIES KNOWLEDGE INCLUDING TREATMENT PLANNING STATES AND ACTIONS

CROSS REFERENCE TO RELATED APPLICATION

This application claims priority to U.S. Patent Provisional Application No. 62/845,942, filed May 10, 2019, and titled SYSTEMS AND METHODS FOR LEARNING AND ACCUMULATING OPTIMAL STRATEGIES FOR RADIATION TREATMENT PLANNING, the content of which is incorporated herein by reference in its entirety.

FEDERALLY SPONSORED RESEARCH OR DEVELOPMENT

This invention was made with government support under grant number R01CA201212 awarded by National Institutes of Health (NIH). The government has certain rights to this invention.

TECHNICAL FIELD

The presently disclosed subject matter relates generally to radiation therapy. Particularly, the presently disclosed subject matter relates to radiation treatment planning based on a model of planning strategies knowledge that include planning states and planning actions.

BACKGROUND

Radiation therapy, or radiotherapy, is the medical use of ionizing radiation to control malignant cells. Radiation treatment planning is the process in which a team consisting of radiation oncologists, medical physicists and medical dosimetrists plan the appropriate external beam radiotherapy or internal brachytherapy treatment for a patient with cancer. The design of a treatment plan, including a set of treatment parameters, aims to reach an optimal balance of maximizing the therapeutic dose to the tumor target (i.e., plan target volume or PTV) while minimizing the dose spills (i.e., radiation induced toxicity) to the surrounding Organs-At-Risk (OARs). Current treatment planning performed by a human planner is very difficult and time consuming. For example, some complex cases can take several hours to complete. Further, the quality may not be consistent. The lack of consistent quality can be attributed to both insufficient time in searching for best parameters of a plan, and lack of experience in how to search for best parameters.

Radiation treatment planning involves complex decision making in specifying optimal treatment criteria and treatment parameters that take into account all aspects of patient conditions and treatment constraints and also in utilizing the most appropriate optimization algorithms and parameters to reach an optimal treatment plan. It is desired that the plan achieves maximal tumor control while minimizing normal tissue damage. Decision support is needed for treatment criteria, treatment parameters, and often the trade-offs and interplays between the various treatment criteria and corresponding treatment plan parameters. The well designed and dynamically adapted optimization strategies lead to a high quality treatment plan, and that leads to high quality radiation treatment for the specific patient.

Treatment planning, such as pancreas radiotherapy planning, is currently an iterative and interactive process. The planning process typically starts with a planner setting initial optimization constraints/parameters to the PTV and OARs and implanting steps for dynamically evaluating and adapting those parameters to best realize the physician's treatment objectives/criteria. Therefore, the planner may need to adjust the intermediate plan multiple times over the optimization process. Due to the toxicity concerns of gastrointestinal (GI) structures and their close distances to the PTVs, planners usually rely on a trial-and-error approach and repetitively interact with the treatment planning system's (TPS) optimization engine to obtain clinical optimal plans. This process can be time-consuming, and the resultant plan quality may be highly subjective to planner experience.

While there are decision support tools for selecting treatment options, such as selecting surgery, chemotherapy, or radiation therapy as well as for clinical treatment objectives/criteria (i.e., prescription dose to PTV and dose constraints to OARs), there is a desire to provide systems and techniques for radiation therapy decision making in the treatment planning.

BRIEF DESCRIPTION OF THE DRAWINGS

Figure 1:
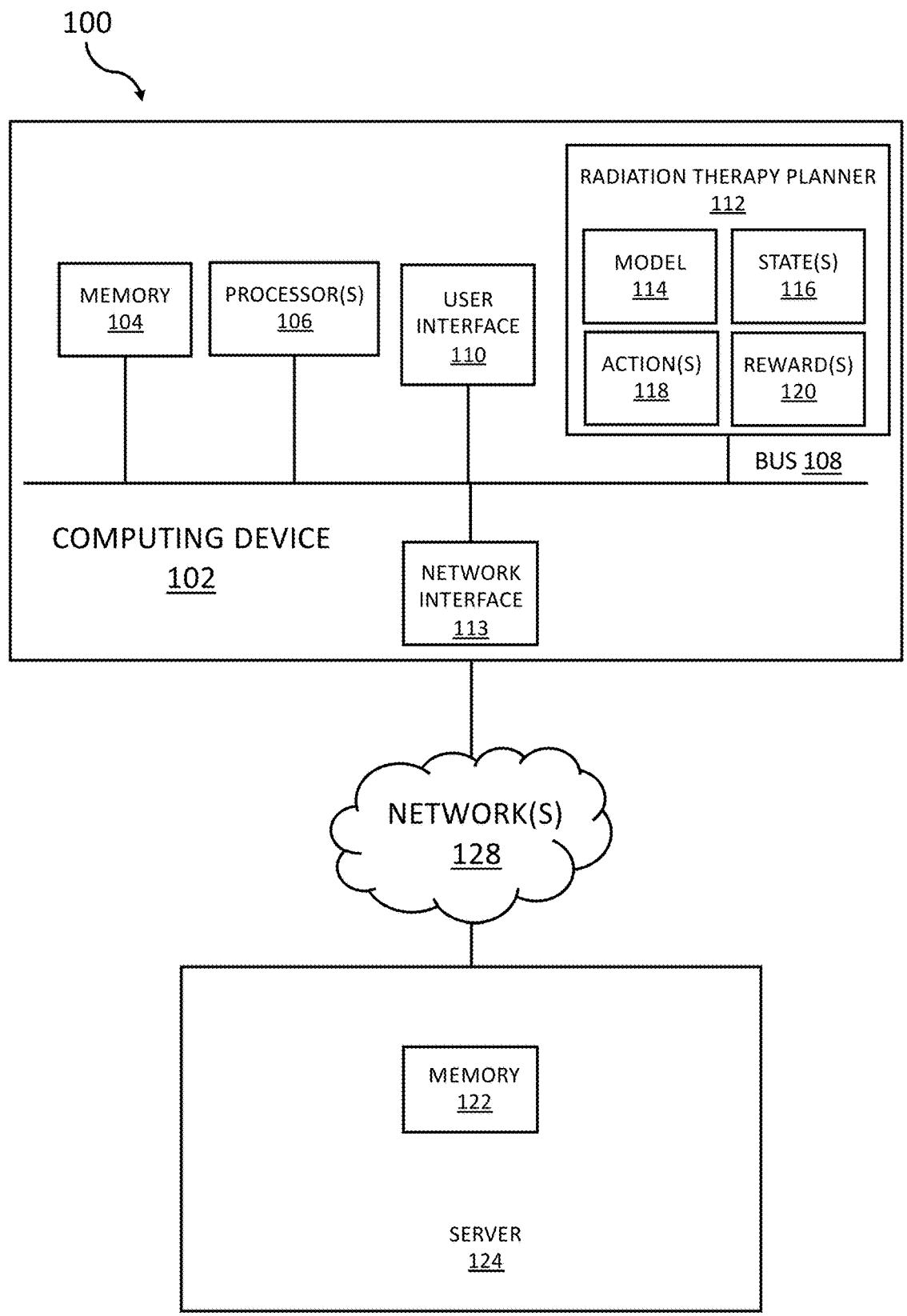
Figure 3:
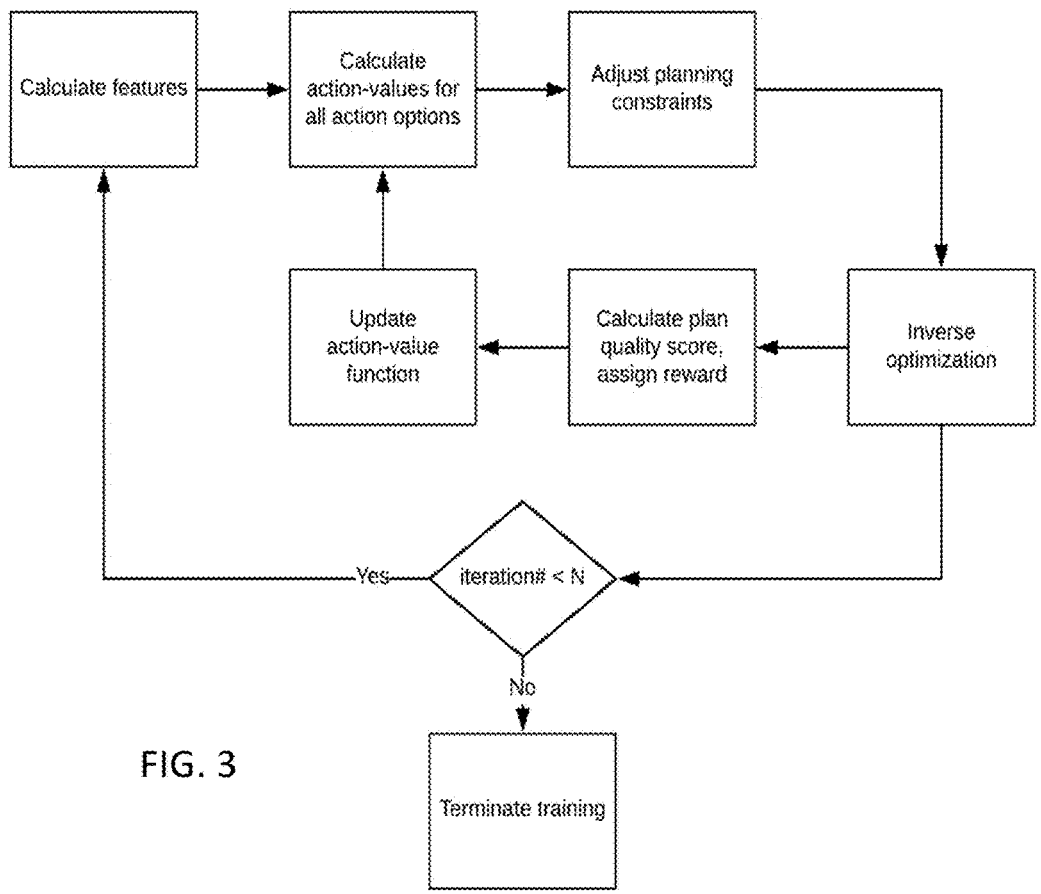
Figure 4:
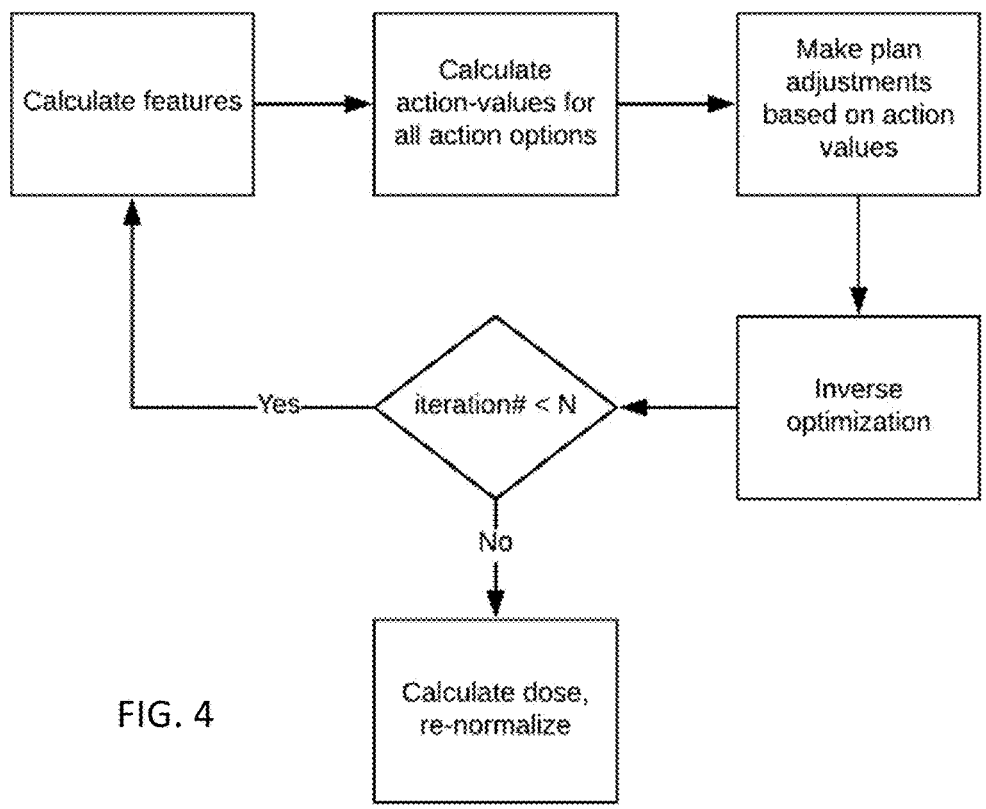
Figure 5:
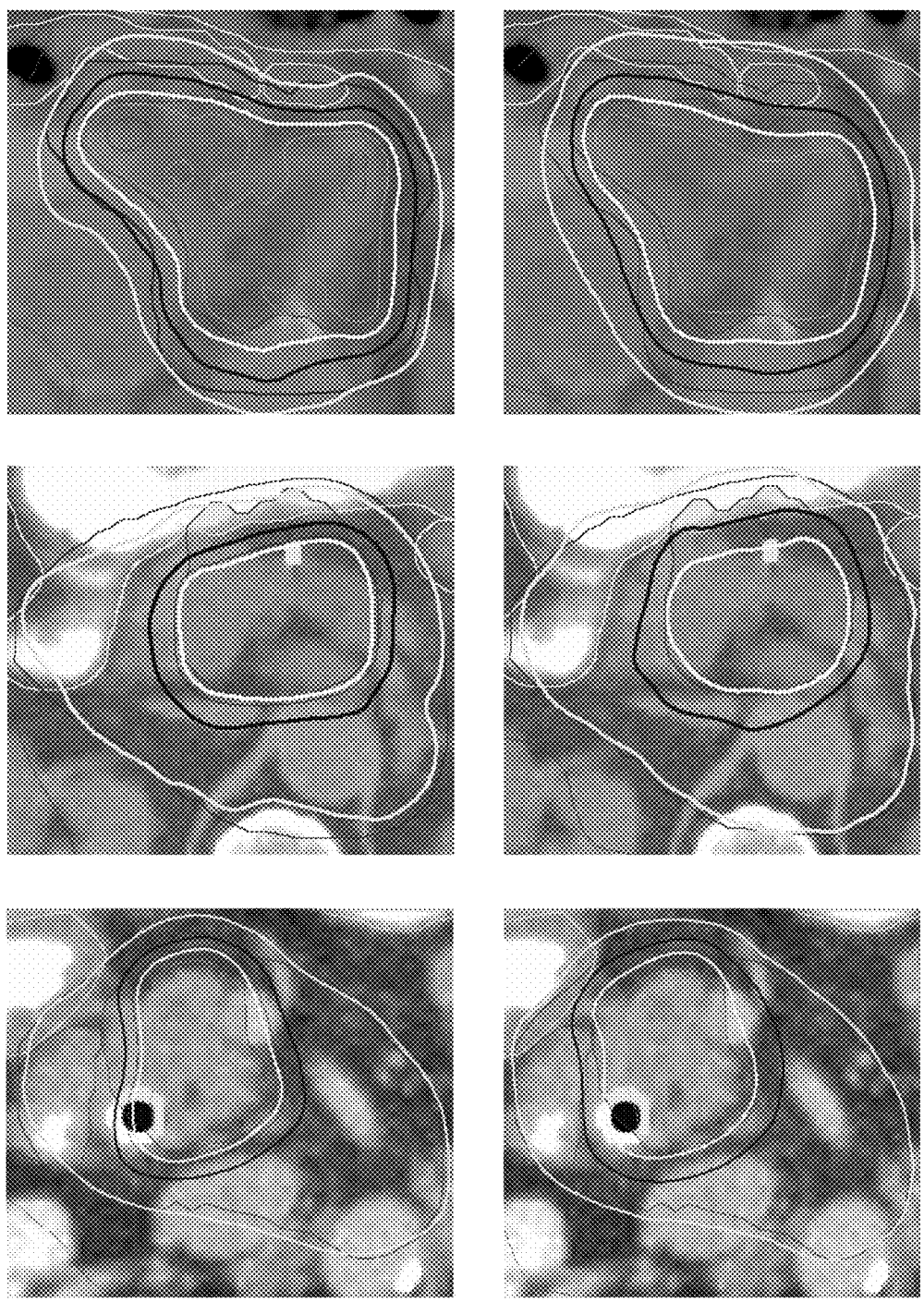
Figure 6:
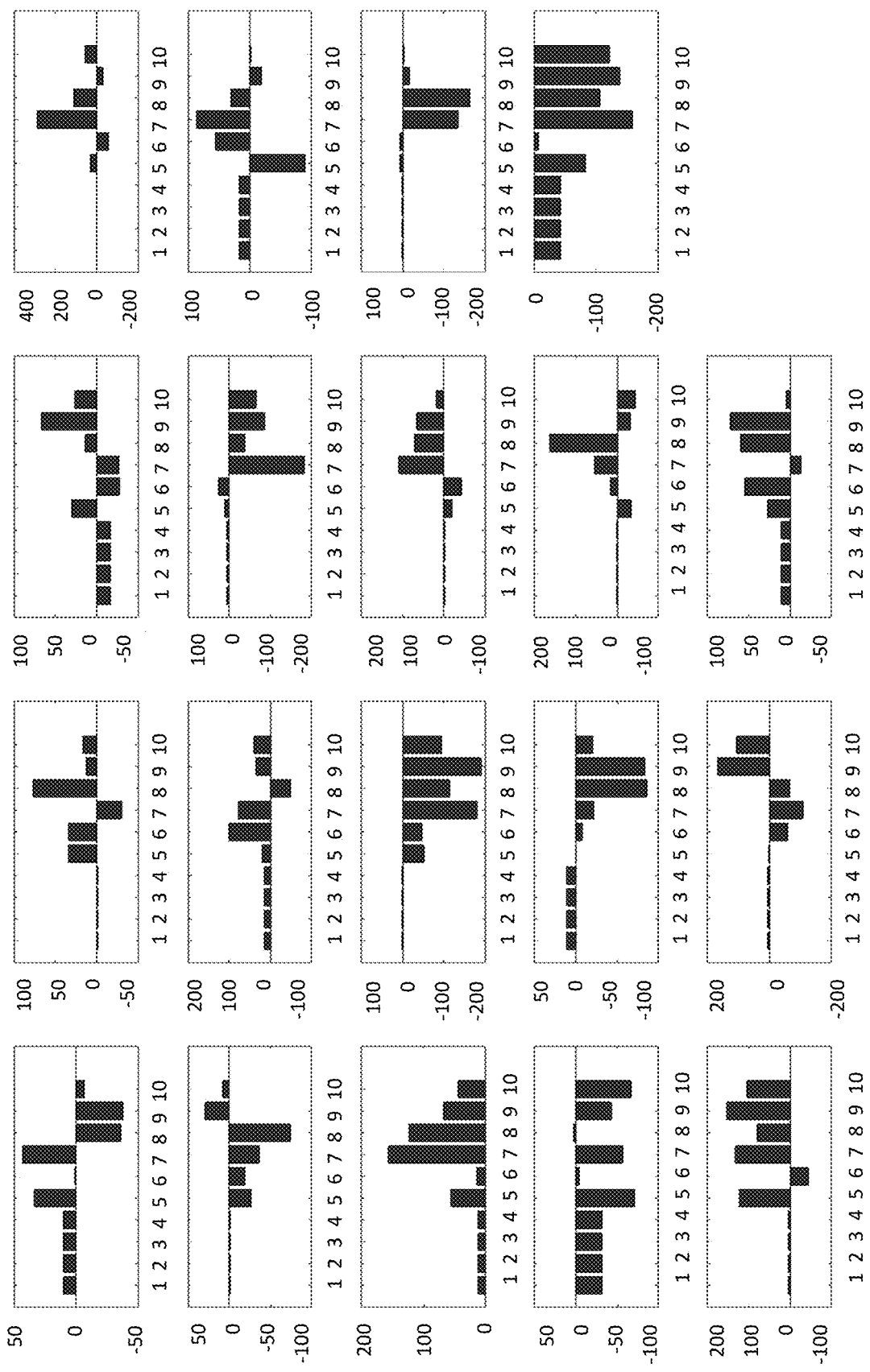
Figure 7:
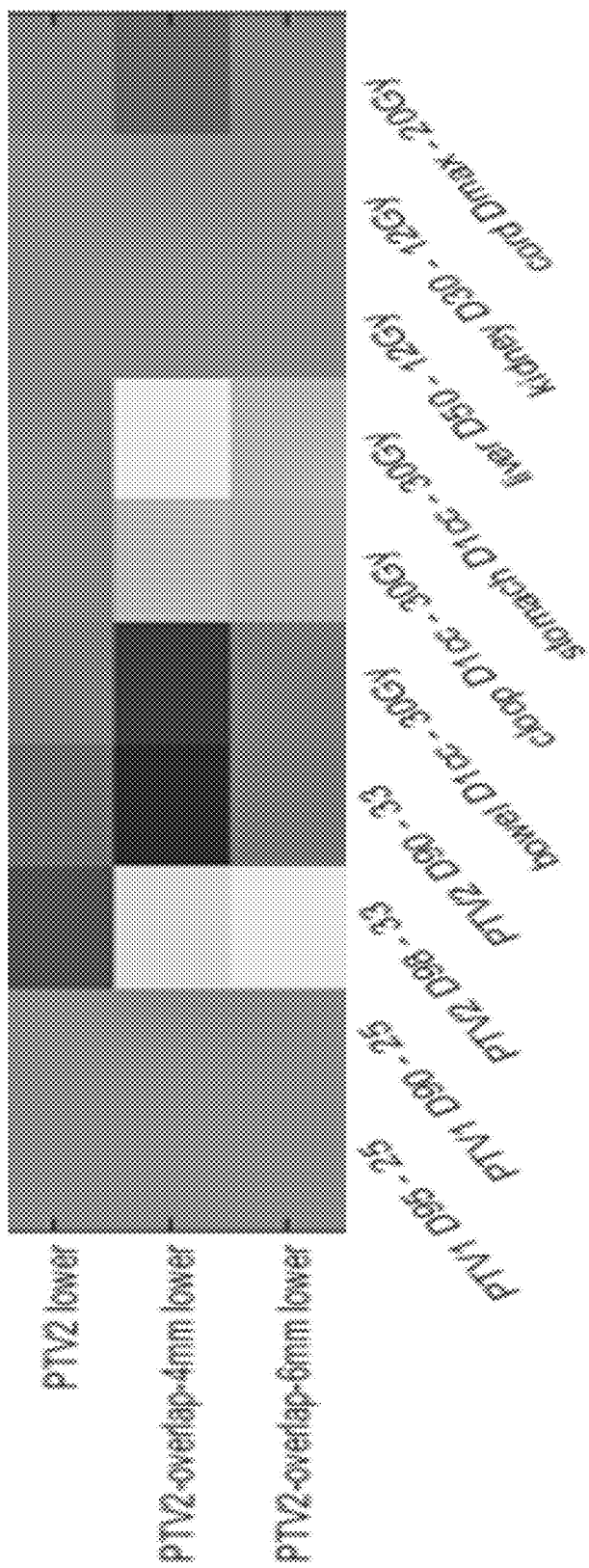
Figure 8:
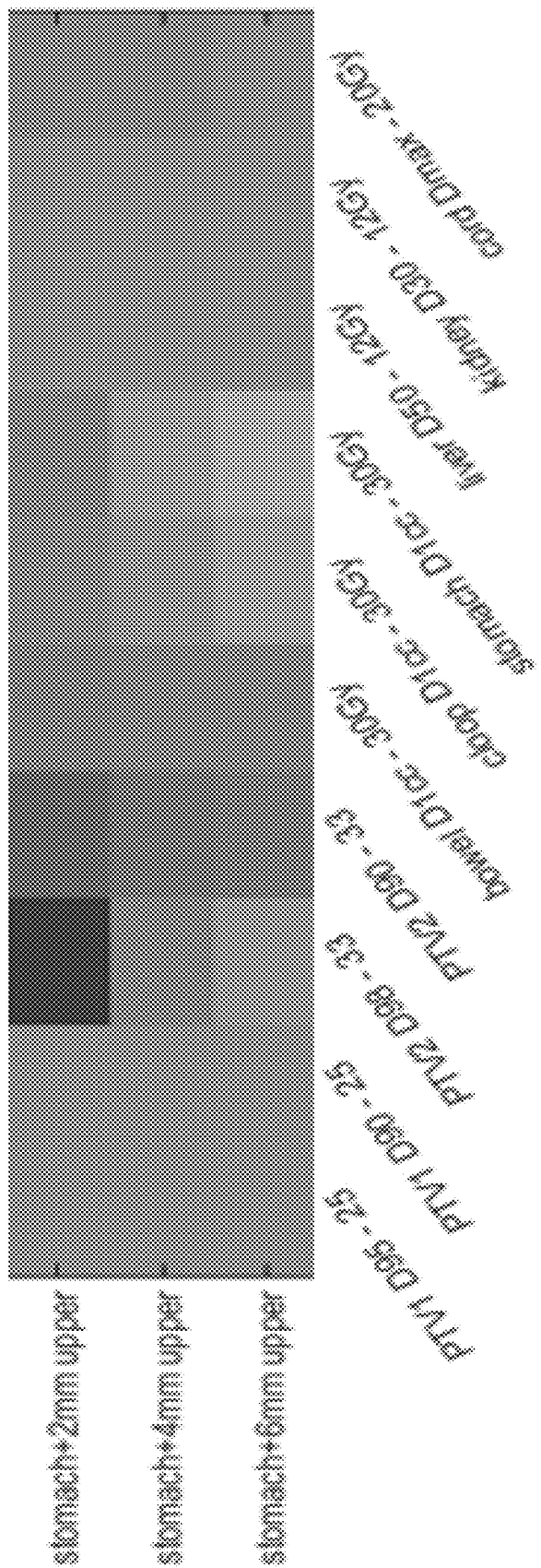
Figure 9:
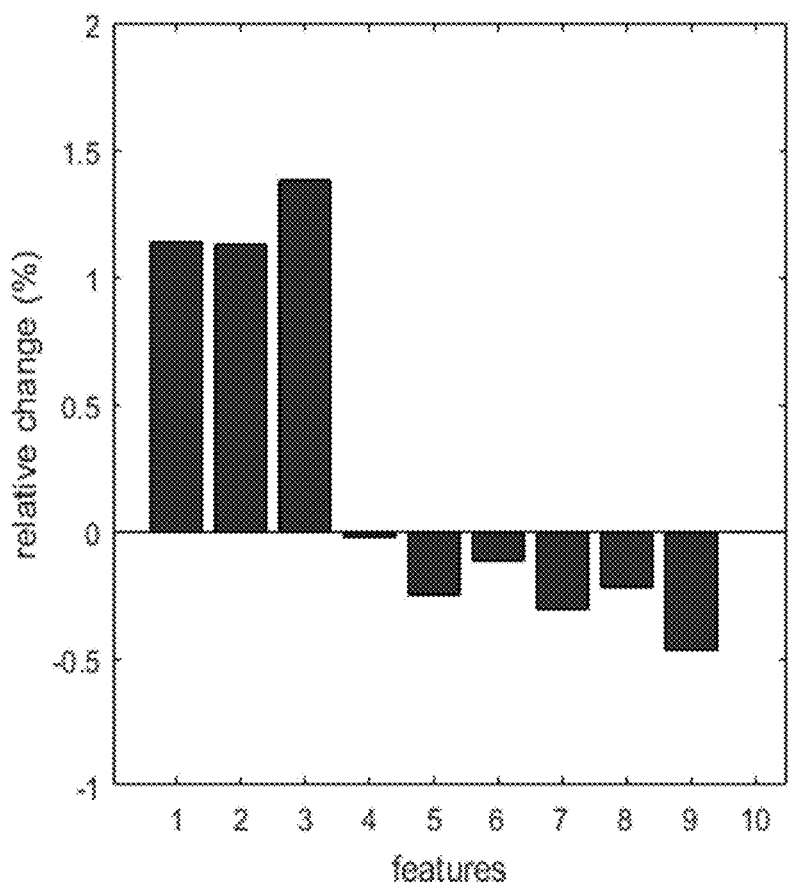
Figure 10:
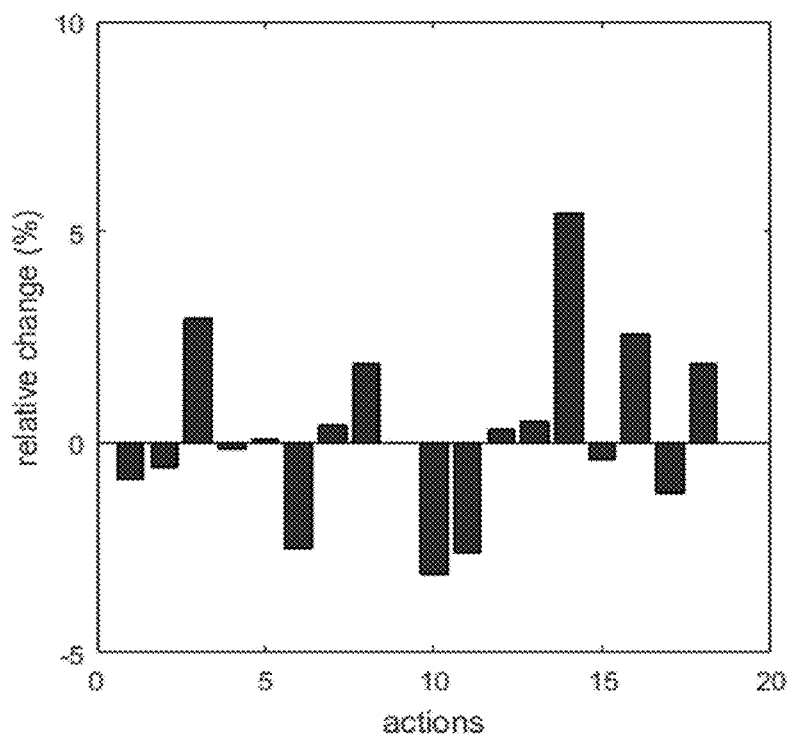
Figure 11:
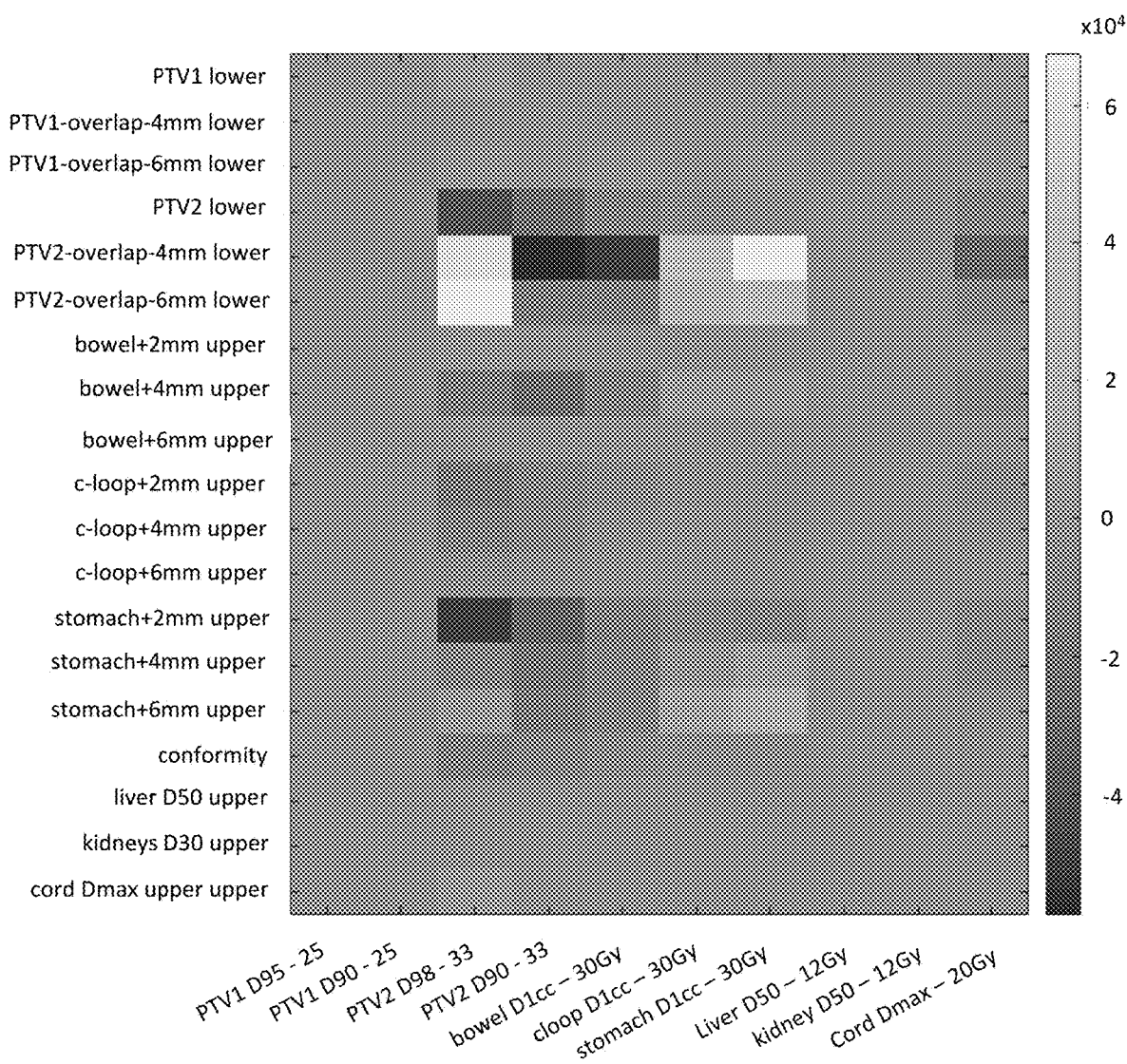

Having thus described the presently disclosed subject matter in general terms, reference will now be made to the accompanying Drawings, which are not necessarily drawn to scale, and wherein:

FIG. 1 is a block diagram of an example system for radiation therapy planning in accordance with embodiments of the present disclosure;

FIGS. 2A-2D are images depicting planning strategies knowledge accumulation on example pancreas stereotactic body radiotherapy (SBRT) cases;

FIGS. 3 and 4 illustrate flow diagrams of an example RL planning framework for a training phase and a validation/application phase, respectively, in accordance with embodiments of the present disclosure;

FIG. 5 depicts images showing dose distributions of three randomly selected validation plans (right column) and their corresponding clinical plans (left column);

FIG. 6 are graphs showing some insight into the RL agent's decision-making process;

FIGS. 7 and 8 show two regions of a reshaped variable $\theta^T$ of a model;

FIGS. 9 and 10 are graphs that show the average knowledge map differences in two different training sessions; and FIG. 11 shows a full weighting vector in the planning strategies model learned by the planning bot after a training session.

SUMMARY

The presently disclosed subject matter includes systems and methods for radiation treatment planning (radiation treatment optimization) based on a model of planning strategies knowledge that include planning states and planning actions. According to an aspect, a method includes receiving anatomical and geometrical characterization data of a target volume for radiation treatment of a patient. The method also includes receiving anatomical and geometric characterization data of at least one organ at risk proximate the target volume. Further, the method includes constructing a model for applying a predetermined radiation dosage to the target volume based on the received data. The model includes planning states and associated planning actions selectable to implement at each state. Each planning action is associated with a reward based on radiation treatment knowledge data. The model is constrained by predetermined limits of radiation dosage to the at least one organ at risk. The method includes presenting information about at least one planning state, the planning actions associated with the at least one planning state, and the rewards associated with the planning actions associated with the at least one planning state. Further, the method includes receiving selection of a planning action associated with the one or more of the planning states. The method also includes reconstructing the model based on the received selection of the planning action.

DETAILED DESCRIPTION

The following detailed description is made with reference to the figures. Exemplary embodiments are described to illustrate the disclosure, not to limit its scope, which is defined by the claims. Those of ordinary skill in the art will recognize a number of equivalent variations in the description that follows.

Articles "a" and "an" are used herein to refer to one or to more than one (i.e. at least one) of the grammatical object of the article. By way of example, "an element" means at least one element and can include more than one element.

"About" is used to provide flexibility to a numerical endpoint by providing that a given value may be "slightly above" or "slightly below" the endpoint without affecting the desired result.

The use herein of the terms "including," "comprising," or "having," and variations thereof is meant to encompass the elements listed thereafter and equivalents thereof as well as additional elements. Embodiments recited as "including," "comprising," or "having" certain elements are also contemplated as "consisting essentially of" and "consisting" of those certain elements.

As used herein, the transitional phrase "consisting essentially of" (and grammatical variants) is to be interpreted as encompassing the recited materials or steps "and those that do not materially affect the basic and novel characteristic(s)" of the claimed invention. See, In re Herz, 537 F.2d 549, 551-52, 190 U.S.P.Q. 461, 463 (CCPA 1976) (emphasis in the original); see also MPEP § 2111.03. Thus, the term "consisting essentially of" as used herein should not be interpreted as equivalent to "comprising."

Recitation of ranges of values herein are merely intended to serve as a shorthand method of referring individually to each separate value falling within the range, unless otherwise indicated herein, and each separate value is incorporated into the specification as if it were individually recited herein. For example, if a range is stated as between 1%-50%, it is intended that values such as between 2%-40%, 10%-30%, or 1%-3%, etc. are expressly enumerated in this specification. These are only examples of what is specifically intended, and all possible combinations of numerical values between and including the lowest value and the highest value enumerated are to be considered to be expressly stated in this disclosure.

Moreover, the present disclosure also contemplates that in some embodiments, any feature or combination of features set forth herein can be excluded or omitted. To illustrate, if the specification states that a complex comprises components A, B and C, it is specifically intended that any of A, B or C, or a combination thereof, can be omitted and disclaimed singularly or in any combination.

Unless otherwise defined, all technical terms used herein have the same meaning as commonly understood by one of ordinary skill in the art to which this disclosure belongs.

As referred to herein, the terms "computing device" and "entities" should be broadly construed and should be understood to be interchangeable. They may include any type of computing device, for example, a server, a desktop computer, a laptop computer, a smart phone, a cell phone, a pager, a personal digital assistant (PDA, e.g., with GPRS NIC), a mobile computer with a smartphone client, or the like.

As referred to herein, a user interface is generally a system by which users interact with a computing device. A user interface can include an input for allowing users to manipulate a computing device, and can include an output for allowing the system to present information and/or data, indicate the effects of the user's manipulation, etc. An example of a user interface on a computing device (e.g., a mobile device) includes a graphical user interface (GUI) that allows users to interact with programs in more ways than typing. A GUI typically can offer display objects, and visual indicators, as opposed to text-based interfaces, typed command labels or text navigation to represent information and actions available to a user. For example, an interface can be a display window or display object, which is selectable by a user of a mobile device for interaction. A user interface can include an input for allowing users to manipulate a computing device, and can include an output for allowing the computing device to present information and/or data, indicate the effects of the user's manipulation, etc. An example of a user interface on a computing device includes a graphical user interface (GUI) that allows users to interact with programs or applications in more ways than typing. A GUI typically can offer display objects, and visual indicators, as opposed to text-based interfaces, typed command labels or text navigation to represent information and actions available to a user. For example, a user interface can be a display window or display object, which is selectable by a user of a computing device for interaction. The display object can be displayed on a display screen of a computing device and can be selected by and interacted with by a user using the user interface. In an example, the display of the computing device can be a touch screen, which can display the display icon. The user can depress the area of the display screen where the display icon is displayed for selecting the display icon. In another example, the user can use any other suitable user interface of a computing device, such as a keypad, to select the display icon or display object. For example, the user can use a track ball or arrow keys for moving a cursor to highlight and select the display object.

The display object can be displayed on a display screen of a mobile device and can be selected by and interacted with by a user using the interface. In an example, the display of the mobile device can be a touch screen, which can display the display icon. The user can depress the area of the display screen at which the display icon is displayed for selecting the display icon. In another example, the user can use any other suitable interface of a mobile device, such as a keypad, to select the display icon or display object. For example, the user can use a track ball or times program instructions thereon for causing a processor to carry out aspects of the present disclosure.

As used herein, "treatment," "therapy" and/or "therapy regimen" refer to the clinical intervention made in response to a disease, disorder or physiological condition manifested by a patient or to which a patient may be susceptible. The aim of treatment includes the alleviation or prevention of symptoms, slowing or stopping the progression or worsening of a disease, disorder, or condition and/or the remission of the disease, disorder or condition.

As used herein, the term "subject" and "patient" are used interchangeably herein and refer to both human and nonhuman animals. The term "nonhuman animals" of the disclosure includes all vertebrates, e.g., mammals and non-mammals, such as nonhuman primates, sheep, dog, cat, horse, cow, chickens, amphibians, reptiles, and the like. In some embodiments, the subject comprises a human.

As referred to herein, a computer network may be any group of computing systems, devices, or equipment that are linked together. Examples include, but are not limited to, local area networks (LANs) and wide area networks (WANs). A network may be categorized based on its design model, topology, or architecture. In an example, a network may be characterized as having a hierarchical internetworking model, which divides the network into three layers: access layer, distribution layer, and core layer. The access layer focuses on connecting client nodes, such as workstations to the network. The distribution layer manages routing, filtering, and quality-of-server (QoS) policies. The core layer can provide high-speed, highly-redundant forwarding services to move packets between distribution layer devices in different regions of the network. The core layer typically includes multiple routers and switches.

As referred to herein, the term "user interface" is generally a system by which users interact with a computing device. A user interface can include an input for allowing users to manipulate a computing device, and can include an output for allowing the computing device to present information and/or data, indicate the effects of the user's manipulation, etc. An example of a user interface on a computing device includes a graphical user interface (GUI) that allows users to interact with programs or applications in more ways than typing. A GUI typically can offer display objects, and visual indicators, as opposed to text-based interfaces, typed command labels or text navigation to represent information and actions available to a user. For example, a user interface can be a display window or display object, which is selectable by a user of a computing device for interaction. The display object can be displayed on a display screen of a computing device and can be selected by and interacted with by a user using the user interface. In an example, the display of the computing device can be a touch screen, which can display the display icon. The user can depress the area of the display screen where the display icon is displayed for selecting the display icon. In another example, the user can use any other suitable user interface of a computing device, such as a keypad, to select the display icon or display object. For example, the user can use a track ball or arrow keys for moving a cursor to highlight and select the display object.

In accordance with embodiments, systems and methods disclosed herein utilize machine learning (ML) and artificial intelligence (AI) technologies for providing intelligent guidance and decisions for healthcare practitioners and planners in the treatment planning process. Such systems and methods can thereby help to reduce average time a physician or planner needs to spend on planning a radiation therapy case as the time consuming iterations and repetitions are performed by ML/AI tools provided by the system. Further, such systems and methods can help to maintain plan quality consistency with the system's and method/s assistance. These tools can help planners design most appropriate, patient specific treatment plans within a short amount of time (e.g., minutes or even seconds) as compared to current fully manual planning process (e.g., 1-4 hours), and therefore ensure best treatment quality for each patient.

The present disclosed subject matter provides techniques that consider explicit acquisition, representation, learning, accumulation of knowledge behind optimal strategies for achieving the desired clinical dose parameters and constraints. Further, the presently disclosed subject matter can provide an AI-based step in treatment planning workflow that specifically and explicitly handles knowledge about planning strategies.

In accordance with embodiments, systems and methods are disclosed herein for acquiring planner experience and knowledge as initial or template strategies and for representing these strategies. These systems and methods may also use rules and/or initial policies in reinforcement learning frameworks.

In accordance with embodiments, systems and methods disclosed herein can learn optimal strategies from multiple pathways, such as prior plan data, empirically formulated planner's experience and knowledge, and guided simulation and search using clinical experience based on reinforcement learning by defining the planning states, planning actions, initial policies, reward function, or a combination of these pathways.

In accordance with embodiments, systems and methods disclosed herein can develop model-based reward functions that are optimal in some sense for clinical experience based reinforcement learning.

In accordance with embodiments, systems and methods disclosed herein provide AI-based techniques for radiation treatment planning. These techniques can include a combination of knowledge-based planning (KBP) models and optimization strategies to provide processes that work effectively for suitable planning scenarios. Example applications include, but are not limited to, complex cases such as pancreac cancer treatment.

In accordance with embodiments, systems and methods disclosed herein provide autonomous treatment planning techniques. Systems implementing such techniques may include a module for acquiring planner experience and knowledge as initial (template) strategies. The systems may also include a module for learning and applying optimal strategies for treatment planning using reinforcement learning. Further, the systems may include a module for learning dosimetric parameter (e.g., dose, DVH, etc.) prediction models from plan data. The systems may also include a module for acquiring new planner experience and knowledge. Further, the systems may include a module for updating dose prediction models. The systems may also include a module for updating strategies with new states, actions, initial policies and reward functions and relearning. Further, the systems may include a control module for coordinating the previous modules and interacting with the users using case-based reasoning as a framework.

FIG. 1 illustrates a block diagram of an example system 100 for radiation therapy planning in accordance with embodiments of the present disclosure. It is noted that functionalities for radiation treatment planning are described in this example as being implemented by a single computing device 102, although it should be appreciated that these functionalities may alternatively be implemented by one or more computing devices located locally together or remote from one another. The computing device 102 may include hardware, software, firmware, or combinations thereof for implementing the described functionalities. For example, the computing device 102 includes memory 104 and one or more processors 106 operatively connected by a bus 108. be implemented by one or more processors and memory. Further, the computing device 102 may include a user interface 110 (e.g., display, mouse, keyboard) for presentation of data and graphics to a user and for receipt of input from the user.

The computing device 100 includes a radiation therapy planner 112 configured to receive geometric characterization data of a target volume for radiation treatment of a patient or subject and to receive geometric characterization data of one or more OARs proximate the target volume. Geometric characterization data of a target or OAR can include one or more of a size, shape, and the like of a volume of the target or OAR. Further, the radiation therapy planner 112 is configured to construct a model 114 for applying a predetermined radiation dosage to the target volume based on the received data (i.e., the geometric characterization data of the target volume and the OAR(s)). The model 114 can include treatment states 116 and associated treatment actions 118 selectable to implement at each state 116. The planner 112 can, for example, construct the model 114 based on one or more of patient image(s), patient organ contour information, target volume contour information, clinical parameters, and the like. Each treatment action 118 can be associated with a reward 120 based on radiation treatment knowledge data. The model 114 can be constrained by a predetermined limit of radiation dosage to the OAR(s). Further, the radiation therapy planner 112 can present (e.g., by use of the user interface 112) to a user information about one or more of the treatment states 116, the treatment action(s) 118 associated with the treatment state(s) 116, and rewards 120 associated with the treatment action(s) associated with the treatment state(s) 116. The radiation therapy planner 112 can also receive (e.g., via the user interface 112) selection of a treatment action 118 associated with the treatment state(s) 116.

In accordance with embodiments, radiation treatment planning involves the determination of various parameters. A parameter may include desired dose parameters and constraints for a particular patient or subject. For example, such parameters and constraints may include, but are not limited to, planning target volume (PTV) dose, organ at risk (OAR) max dose, and the like. Further, treatment plan parameters can be determined that desirably achieve desired dose parameters and constraints. For example, such treatment plan parameters may include, but are not limited to, beam angle, beamlet intensity, and the like.

Systems and methods according to the present disclosure can systematically acquire, represent, learn, and accumulate knowledge for the optimal planning strategies for determining treatment plan parameters that lead to optimal radiation therapy plans. In some embodiments, systems and methods disclosed herein can use machine learning and/or artificial intelligence (AI) techniques. In some embodiments, systems and methods disclosed herein can use manually acquired clinical knowledge summerized as template or as a set of rules/policies using certain dose/DVH thresholds. Moreover, the present disclosure can provide an AI-based process for radiation treatment planning that combines direct rule or protocol based planning strategies for optimization settings, knowledge-based planning (KBP) models and machine learning based planning strategies as disclosed herein. These AI-based systems and methods can work collectively and effectively for all planning scenarios including complex treatment cases such as pancreac cancer treatment.

In embodiments, a system as disclosed herein can be implemented by one or more modules for providing an AI-based autonomous treatment planning. For example, the planner 112 shown in FIG. 1 can include a module for acquiring planner experience and knowledge as initial (template) strategies. Further, the planner 112 can include a module for learning and applying optimal strategies for treatment planning using clinical experience based reinforcement learning. The planner 112 can also include a module for learning dose prediction models from plan data. Further, the planner 112 can include a module for acquiring new planner experience and knowledge. The planner 112 can also include a module for updating dose prediction modele. Further, the planner 112 can include a module for updating strategies with new states, actions, initial policies and reward functions and relearning. The planner 112 can also include a control module for coordinating the previous modules and interacting with the users using case-based reasoning as a candidate framework.

Clinical sites and cases that present complex radiotherapy treatment planning scenarios and goals often require applications of many sources of knowledge for realizing optimal treatment plan parameters, and many iterative adjustments of optimization parameters during an iterative planning process. For example, the target volume (or planning target volume) may have overlaps with surrounding OARs, and the prescription dose to the target volume may be higher than OARs' tolerant doses.

Analogous to the "autonomous-driving" scenario, the target volume coverage often has to "yield" to the dose limit to avoid the surrounding OARs, however, it is not a "full stop". Rather, it may be a dynamic adjustment depending on the breathing motion range and corresponding motion management in place for the particular patient, the size and extent of the gross tumor volume (GTV), the prescription dose-fractionation scheme, the patient's specific anatomy, and other concerns on the dose limit of the OARs. Therefore, the target volume coverage often is not a uniform dose distribution but a staged multi-level dose coverage taking into account multiple radiation physics rules and clinical treatment factors.

In accordance with embodiments, a set of treatment criteria and actions may be applied in dealing with conflicting goals of treatment planning. Systems and methods disclosed herein can assist with adapting or balancing the impact of these treatment goals/objectives for each patient. Although the basic principles of treatment criteria and actions may be clear or can be made into a template for planning reference, the presently disclosed systems and methods can apply various criteria, actions and knowledge for optimizing a radiation treatment plan for cases such as pancreas SBRT (or spine SBRT). For example, in a spine SBRT NRG Oncology RTOG 0631 clinical trial, general treatment criteria were listed, however, planner experience and knowledge played a significant role in the final quality of the submitted plans. For all plans approved at pre-treatment review and subsequently treated in the study (which means they met most of the general treatment criteria), 26 percent of cases had minor deviations in target coverage (one of the treatment criteria) and 26 percent had variations in normal tissue doses (one of the treatment criteria). Using knowledge-based planning models as a planning assistance tool, the study found no statistically significant differences in conformity or gradient indices (one of the treatment criteria) between the manually optimized plans and the KBP plans. However, they found that the volume of PTV receiving prescription dose increased from $93.3 \pm 3.2\%$ to $99.5 \pm 0.7\%$ ($P<0.001$) when using KBP. In such example, AI-agent or ML models help the treatment plan getting closer to one of the treatment criteria (PTV coverage) without worsing of meeting other treatment criteria.

Unlike multi-criteria optimization (MCO) where the constraints are assumed known ahead of time and decisions on tradeoff are made after plans are blindly generated, tradeoff decisions of many complex treatment scenarios, such as pancreas SBRT, may optimally be made during planning where additional constraints may be introduced dynamically. One of example is purposely staggering the high dose regions in areas of the PTV that is close to OARs with very stringent dose limits. Reinforcement learning in accordance with systems and methods disclosed herein can provide solutions to challenges present in complex treatment scenarios such as pancreas SBRT planning. The general idea of reinforcement learning is that, through a large number of repetitive interactions with the treatment planning system (TPS) environment, an autonomous agent can learn to make appropriate adjustment actions (staggering the dose as mentioned above) given certain state (overdose in the OAR regions very close to PTV as mentioned above) of the current planning process. When the learning process (or training) is finished, the agent can provide an action (e.g., set forth as an action 118 in FIG. 1) indicating a plan adjustment to take for any situation (e.g., set forth as a state 116 in FIG. 1), similar to an experienced human planner. This implementation, or the final decision model (e.g., set forth as a model 114 in FIG. 1), can be the process used by a healthcare practitioner for radiation therapy planning of a patient. The presently disclosed systems and methods can manage the large number and complexities of treatment planning states and actions of a radiation therapy planning scenario, while also managing constraints discussed herein.

Treatment planning knowledge can be accumulated and collected via personal training and experience and published clinical trial study data or clinical treatment plan data. The presently disclosed subject matter can learn strategies for radiation treatment planning based on discovering, describing, extracting, and integrating planning knowledge and experience from multiple comprehensive knowledge sources. For example, such data may be stored in memory 104 of the computing device 102 shown in FIG. 1 or retrieved from memory 122 of a remote server 124. For example, the planner 112 may use a network interface 126 of the computing device 102 to access and retrieve, via one or more networks 128, the data stored in memory 122 of the server 124

Patient information may include any information that may influence a healthcare practitioner's decision on prescribing dose to a target volume and each of the OARs. Example patient information includes, but is not limited to, the patient's previous radiation treatment, prior treatment dose, location, and the dose volume information of the prior treatment to each of the OARs, patient's physiological conditions such as organ function analysis, transplant condition, and the like.

In accordance with embodiments, models disclosed herein can allow the prediction of dose and dose volume histogram of the patient. Further, the system can utilize a generalized case-based reasoning mechanism to allow selection of different models based on one or more clinical conditions that may be relevent to the patient.

Figure 2A:
Figure 2B:
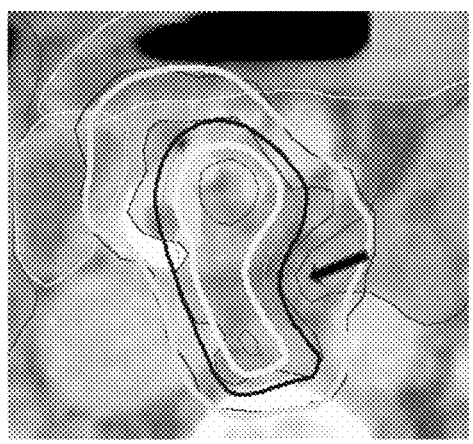
Figure 2C:
Figure 2D:
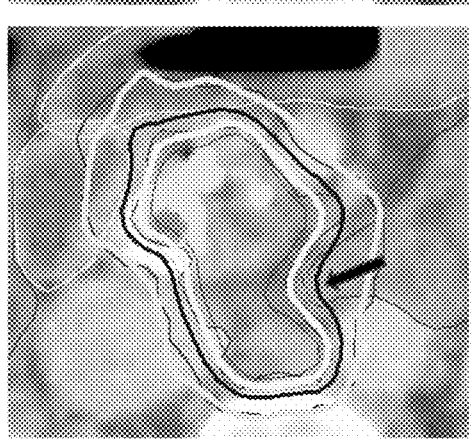

FIGS. 2A-2D are images depicting knowledge accumulation on example pancreas stereotactic body radiotherapy (SBRT) cases. Particularly, FIG. 2A shows a clinical plan. FIG. 2B shows a first epoch. FIG. 2C shows a fifth epoch. FIG. 2D shows a tenth epoch. The prescription doses to the primary PTV and the boost PTV are 25 Gy and 33 Gy, respectively.

The ultimate goal is to improve treatment planning efficiency (using ML/AI tools to replace some human planner's iterative operations) and consistency (using ML/AI tools to supplement the human planer's search for best planning parameters in very short time ensures improved opportunity to find the best solution for each patient's particular anatomy and condition) by optimizing clinical workflow.

In embodiments, systems and methods according to the present disclosure provides for the development of Clinical Experience Guided Reinforcement Learning (CEGRL) techniques to address the challenges in complex planning scenarios such as pancreas SBRT planning. By leveraging the clinical knowledge and actions of experienced planners from various sources, the search space in reinforcement learning can be significantly reduced and can guide the learning of effective policies within manageable amount of time and computing resources.

There are multiple approaches to incorporating clinical experience into reinforcement learning. In embodiments, clinical experience can be used to limit the state and action spaces. There are multiple algorithms for performing reinforcement learning. An example reinforcement learning algorithm is the Q-learning algorithm, which updates the knowledge ("quality" assessment) of the agent sequentially, one state-one action at a time according to the Bellman equation or one of its variations. Given enough training samples and training time, Q-learning can converge to an optimal planning or action solution. Additionally, in order to ensure that the entire planning process functions optimally, techniques for setting up other plan parameters such as the VMAT arc range, field size, and collimator angle may be used.

In some embodiments, systems and methods disclosed herein may be hosted on one or more servers through a network. In other embodiments, the users (e.g., medical providers) may provide inputs at a graphical user interface for the system to build the one or more predictive models (e.g. treatment plans). In another embodiment, the users (e.g., medical providers) can interact with the system as provided herein through a number of ways, such as over one or more networks. In such embodiments, one or more servers accessible through the network(s) can host the treatment planning system. The one or more servers can also contain or have access to the one or more data stores for storing data for the treatment planning system, or receive input data from external sources. It should be appreciated that in alternative embodiments, the server may be self-contained and not connected to external networks due to security or other concerns.

In accordance with embodiments, the present disclosure provides methods for automatic IMRT Planning Via Static Field Fluence Prediction (AIP-SFFP) and deep learning techniques for real-time treatment planning. In embodiments, AIP-SFFP generates a IMRT plan through predictions of fluence maps using the patient anatomy. This can be achieved without inverse optimization. AIP-SFFP centralizes a custom-build deep learning network, Dense-Res Hybrid Network (DRHN), which contains both DenseNet and ResNet implementations in a cascade architecture. Predictions from DRHN are imported into a treatment planning system such as the ECLIPSE™ system (Varian Medical Systems, Palo Alto, Calif.) for dose calculation and plan generation. AIP-SFFP was demonstrated for prostate IMRT simultaneously-integrated boost (SIB) planning (58.8 Gy/70

Gy to PTV58.8/PTV70 in 28fx). Training data was generated from 105 patients using a 9-beam field template on a knowledge-based planning (KBP) platform based on ECLIPSE™ scripting interface (ESAPI). The following images at each field angle were stacked as inputs for DRHN training: 1) 2D contour projections of PTVs and organs-at-risk (bladder/rectum); 2) digital reconstructed radiographs (DRRs) of CT attenuation coefficients. 10-fold validation was implemented during training. 7 patients were used as independent tests of AIP-SFFP. The generated plans were evaluated by key dosimetric parameters derived from institutional guidelines. After dose normalization (PTV70 V70 Gy=95%), all 7 AIP-SFFP test plans achieved excellent target coverages (PTV58.8 V58. 8 Gy=98.3±1.8%). Isodose distributions were conformal outside of PTVs with acceptable heterogeneity inside PTV70. 3D max dose values were D0.1 cc=106.5±0.5%. Maximum dose to rectum (D0.1 cc=72.4±0.6 Gy) and bladder (D1 cc=71.6±1.1 Gy) showed excellent organs-at-risk sparing. V70 Gy and V65 Gy of rectum and bladder from all 7 plans also met institutional guidelines. Each test plan was generated with 15 seconds or less including prediction and dose calculation. This indicates the feasibility of real-time planning with direct fluence map prediction. AIP-SFFP was successfully developed and demonstrated good overall plan qualities and real-time efficiency in prostate SIB.

In accordance with embodiments, systems and methods disclosed herein use reinforcement learning to systematically address complex tradeoffs and physician preferences for pancreas SBRT treatment planning. The focus of pancreas SBRT planning is finding a balance between gastrointestinal OARs sparing and planning target volume coverage. Planners evaluate dose distributions and make adjustments in order to optimize planning target volume coverage while adhering to OAR dose constraints. Such interactions between the planner and the treatment planning system have been formulated into a finite-horizon reinforcement-learning (RL) model. First, the planning states that represent the current status of treatment plan and planning parameters are discretized in a similar fashion to how planners evaluate plans (e.g., constraint satisfaction, target coverage). Second, steps that planners can implement to address different planning needs are defined as planning actions. Third, a "reward" system has been developed based on physician knowledge and experience. Subsequently, machine learning is implemented as a state-action-reward-state-action (SARSA) reinforcement learning process with limited dimensionality to ensure convergence and performance. The RL system was trained with 14 plans, cycling with 20 epochs, each of which consisted of 15 sequential agent-TPS interactions. The RL agent then planned 16 cases in a separate validation set. The RL agent took 18 minutes to plan each validation case, in contrast to 1-2 hours of manual planning. All 16 clinical plans and 16 RL plans meet pre-defined GI constraints (V30 Gy<1 cc). The differences between primary PTV coverage of RL plans (98.9%±0.5%) compared to clinical plans (97.6%±0.7%) are significant (paired-sample t-test, p=0.006), while simultaneous integrated boost PTV coverages are similar for clinical plans (87.6%±4.9%) and RL plans (86.7%±5.2%) (p=0.63). The reinforcement learning process is capable of capturing planner experience and prior knowledge of pancreas SBRT planning. This study demonstrated that the performance of the RL agent is comparable to that of human planners with much more efficient planning time.

In accordance with embodiments, a method for atlas-guided fluence initialization and optimization are disclosed and demonstrated for pancreas SBRT. Respecting luminal OAR constraints while maximizing target coverage can be challenging for pancreas SBRT due to adjacency of the structures. Resultant plan quality is dependent on planner's experience. To improve plan quality consistency, optimal fluence can be deduced from previous plans with similar anatomy. A study was conducted to investigate the feasibility of using atlas matching to initialize and accelerate fluence optimization for pancreas SBRT. Thirty patients treated with pancreas SBRT were included. To build the atlas, the contours of PTV and duodenum (OAR) were first extracted. All axial contour slices were categorized into three groups based on the minimum PTV-OAR distance d_min: PTV-only, adjoining/adjacent OAR (d_min≤10 mm), and distant OAR (d_min>10 mm). Then, baseline 9-field IMRT plans using uniformly-initialized fluence were generated using an in-house optimizer. To find the query's best matched atlas, a scoring system defining anatomy similarity metrics was developed. The atlas case's fluence was transferred to the query PTV with scaling and set as the initial fluence. The atlas-guided fluence optimization proceeded with the same constraints for the query case. A leave one-out cross validation was performed to assess the feasibility of the proposed strategy. The atlas-guided plans were compared with uniformly-initialized plans in terms of cost function values and dosimetric endpoints. Paired t-test was performed. Atlas-guided fluence optimization reduced the mean initial cost function value by 69.7% (p<0.01). For dosimetric endpoints, the average OAR mean dose and PTV V100% were 14.07 Gy and 37.1% for atlas-guided plans, and 14.21 Gy (p<0.01) and 35.7% (p<0.01) for uniformly-initialized plans. Results showed feasibility to use prior fluence from plans with similar anatomical patterns to guide pancreas SBRT fluence optimization. It offered customized initialization which achieved improved dosimetric endpoints. This fluence optimization scheme may reduce inter-planner quality variation.

In accordance with embodiments, systems and methods disclosed herein can be utilized for any radiation treatment scenarios and cancer sites. They are especially advantageous for complex treatment scenarios such as the pancreas stereotactic body radiotherapy (SBRT) treatment planning. Such planning can require planners to make sequential, time consuming changes in the treatment planning system. Systems and methods disclosed herein can use a reinforcement learning-based automated planning tool to systematically address complex tradeoffs and achieve consistent high plan quality efficiently. The focus of pancreas SBRT planning is finding a balance between gastrointestinal OAR sparing and planning target volume coverage. Planners evaluate dose distributions, making adjustments in order to optimize PTV coverage while adhering to OAR dose constraints. In embodiments, such interactions between the planner and the treatment planning system have been formulated into a finite-horizon reinforcement-learning model. First, planning states that represent the status of treatment plans and planning parameters can be evaluated similar to how planners evaluate plans. Second, steps that planners for addressing different planning needs can be defined as planning actions as disclosed herein. Third, a "reward" system may be derived based on an objective function guided by physician input. Finally, the planning task can be formulated as a state-action-reward-state-action (SARSA) RL model. In experiments, the RL system was trained with 48 plans augmented from 16 previously treated patients. The RL agent then planned 24 cases in a separate validation set.

In experiments, the planning agent according to systems and methods disclosed herein generated clinically acceptable plans for all 24 validation cases. Additionally, it was found that the average feature patterns and the corresponding actions are distinct, demonstrating that the agent takes consistent and predictable actions. More importantly, the knowledge maps learned by the RL agent are in line with human planning knowledge, and the knowledge maps learned in separate training sessions are consistent.

It has been demonstrated that the training phase of our planning agent is tractable and reproducible, and the knowledge obtained by the agent is interpretable. As a result, the trained planning agent can be validated by human planners and serve as a robust planning routine in the clinics.

Treatment planning, especially pancreas SBRT planning, is an iterative and interactive process. The planning process starts with a planner setting initial optimization constraints to the PTV and OARs and executing the optimization algorithm embedded in the treatment planning system. The set of initial optimization constraints may not generate the optimal plan, considering anatomy variations from case to case. Therefore, the planner may iteratively adjust the optimization objectives to make it clinically optimal. Due to the toxicity concerns of the GI structures and their minimal distances to the planning target volumes, planners can rely on a trial-and-error approach and repetitively interact with the TPS to achieve such clinical optimality. This process can be time-consuming, and the resultant plan quality may be highly subjective to planner experience.

Reinforcement learning can offer a potential solution to this problem. In reinforcement learning, a computer algorithm, or agent, gains decision making knowledge by repetitively interacting with the environment and evaluating rewards (improvement of the plan dose distribution) associated with the action (changing of optimization objectives). Utilizing the concept of reinforcement learning, through repetitive interactions with the TPS, an artificial, autonomous agent can learn to make appropriate adjustments given anatomy information and intermediate planning results, and ultimately design clinically optimal plans. When the training process is finished, the agent knows what plan adjustments (i.e., action) to take for any situation (i.e. state).

The treatment planning of pancreas SBRT can be time-consuming. Although the treatment planning system can optimize plans with respect to the objective function given by the planner, the setting of objective function can be highly dependent on the shape, size, and location of the PTVs. Planners usually interact with the TPS multiple times and perform actions including adjusting dose-volume constraints and create necessary auxiliary structures in order to get desirable dose distributions. State-action-reward-state-action (SARSA), also known as connectionist Q-learning, can perform well when used in accordance with the presently disclosed subject matter. It is an efficient, sampling-based, model-free algorithm that changes the knowledge of the agent sequentially based on the interactive training process. A SARSA-based treatment planning module is provided that assists planners to efficiently achieve consistent and high-quality plans for pancreas SBRT. A state-action-reward-state-action (SARSA) reinforcement-learning framework is disclosed to address this issue systematically. An example formulation of SARSA is as follows:

$$Q^{new}(s,a) \leftarrow Q^{old}(s,a) + \alpha \cdot [r(s,a,s') + \gamma \cdot Q^{old}(s',a') - Q^{old}(s,a)],$$

where s and a denote current state and action; s' and a' denote next state and action; $Q^{old}$ and $Q^{new}$ denote the value function before and after the update; r denotes the immediate reward; $\alpha$ denotes the learning rate of the agent; and $\gamma$ denotes the discount factor of the system.

With linear function approximation (LFA), the action value function of the treatment planning RL problem can be defined with the following equation:

$$Q_\theta(s,a) = \theta^T \varphi(s,a),$$

where $Q_\theta(s,a)$ represents the expected final score value at state s when action a is taken, $\theta^T$ denote a parameter vector that will be learned through the training process, and $\varphi(s,a)$ is a set of features carefully engineered to reduce the complexity of the reinforcement learning problem without losing out on generalization. In our implementation, the feature $\varphi(s,a)$ is generated as an tensor product of a state vector f(s) and an action vector g(a): $\varphi(s,a) = \text{vec}[f(s) \oplus g(a)]$. Here $\oplus$ denotes the Kronecker tensor product operator. f(s) is formulated as $f(s) = [1, \Delta D_1, \Delta D_2, \ldots, \Delta D_{N_1}, \Delta V_1, \Delta V_2, \ldots V_{N_2}]^T$, where $\Delta D_n = \overline{D}_n - D_n$ and $\Delta V_n = \overline{V}_n - V_n$ denote the differences between the predicted/estimated dose constraints and the actual dose/volume value at the current iteration. The state vector f(s) is evaluated in two sections: $\Delta D_{n_1}$, $n_1 \in [1, 2, 3, \ldots, N_1]$ denotes the dose values evaluated (e.g. stomach $D_{max}$); $\Delta V_{n_2}$, $n_2 \in [1, 2, 3, \ldots, N_2]$ denotes the volume values often evaluated by physicians (e.g. liver V20). The complete state vector implemented for our pancreas SBRT planning module is listed in the Appendix. The action vector $g(a) = [1(a=A_1), 1(a=A_2), \ldots, 1(a=A_M)]^T$ is essentially an array of M indicators that represent indices of M actions. The M action options are designed based on the actions commonly taken by our clinical planners during pancreas SBRT treatment planning. Note that sequential steps are taken and the vector only has one non-zero component at any steps during the iterations.

In accordance with embodiments, the following algorithm may be implemented:

---

Algorithm 1. Automatic learning of planning strategies with linear function approximation (SARSA-LFA)

Initialize the weighting vector $\theta$.

Set exploration-exploitation factor $\varepsilon$, learning rate $\eta$, discount factor $\gamma$, and max number of interactions per plan N.

Initialize plan, set initial constraints based on a template. Optimize plan.

Run N times

Take actions based on $Q_\theta(s, a)$. Optimize plan.

Evaluate features $\varphi(s', a')$ and reward r.

$Q_\theta(s', a') = \theta^T \varphi(s', a')$ $\delta = r + \gamma Q_\theta(s', a') - Q_\theta(s, a)$ $\theta \leftarrow \theta + \eta \delta \varphi(s, a)$

---

In total, 19 actions are used in this example to ensure the agent has an optimal choice in any given state that may lead to the optimal plan quality. The actions include adding constraints to liver, kidney, cord, and auxiliary structures associated with stomach, duodenum, bowel, and PTV. A list of the actions is given in Table 1. In the table, $\overline{D_{pri}}$ and $\overline{D_{bst}}$ denotes the prescription levels for the primary PTV and the boost PTV.

TABLE 1

Action options for the RL planning program.

| Action index | structure | volume | dose | priority | constraint type |
|---|---|---|---|---|---|
| 1, 2, 3 | $PTV_{pri}$ minus overlapping region with GI OARs with 0 mm, 4 mm, 6 mm expansion | 96% | $\overline{D_{pri}}$ | 80 | Lower |
| 4, 5, 6 | $PTV_{bst}$ minus overlapping region with GI OARs with 0 mm, 4 mm, 6 mm expansion | 96% | $\overline{D_{bst}}$ | 80 | Lower |
| 7, 8, 9 | Bowel with 2 mm, 4 mm, 6 mm expansion | 0.5 cm³ | $D_{1\,cc} - 2$ Gy | 80 | Upper |
| 10, 11, 12 | Duodenum with 2 mm, 4 mm, 6 mm expansion | 0.5 cm³ | $D_{1\,cc} - 2$ Gy | 80 | Upper |
| 13, 14, 15 | Stomach with 2 mm, 4 mm, 6 mm expansion | 0.5 cm³ | $D_{1\,cc} - 2$ Gy | 80 | Upper |
| 16 | $PTV_{pri}$ minus $PTV_{bst}$ | 20% | $D_{20\%} - 2$ Gy | 50 | Upper |
| 17 | Liver | 50% | 12 Gy | 50 | Upper |
| 18 | Kidneys | 30% | 12 Gy | 50 | Upper |
| 19 | Cord | 0 | 20 Gy | 50 | Upper |

The action vector $g(a)=[1(a=A_1), 1(a=A_2), \ldots, 1(a=A_M)]^T$ is an array of M indicators that represent indices of M actions. The M action options are designed based on the actions commonly taken by our clinical planners during pancreas SBRT treatment planning. Since we are taking sequential steps, the vector only has one non-zero component at any step during the iterations. In total, 19 actions are used to ensure the bot has an optimal choice in any given state that may lead to the optimal plan quality. The actions include adding constraints to liver, kidney, cord, and auxiliary structures associated with stomach, duodenum, bowel, and PTV. Full descriptions of the actions are listed in Table 1.

The reward r is decided based on the plan quality score improvement after each step. The plan evaluation score is set as a weighted combination of various clinical plan quality metrics:

$$S = -\sum_i W_i \max(K_i - K'_i, 0) - \sum_j W_j \max(H_j - H'_j, 0)^2,$$

where $K'_i$, $H'_j$ denote prescribed soft and hard constraints and $K_i$, $H_j$: achieved soft and hard constraint values. To keep the notation simple, positive values were assigned to upper constraints (OAR sparing, PTV hotspot, dose conformity) and negative values to lower constraints (PTV coverage). The weights are selected carefully to reflect clinical plan quality preferences, which were consulted and reviewed with physician co-investigators during the experiment design. The current implementation focuses on getting as much target boost coverage as possible while satisfying GI structure $D_{1\,cc}$ dose constraints. This strategy is consistent with some current clinical practice preferences, as the boost PTV prescription dose is likely to be higher for therapeutic gains. Different weightings of the plan quality scores produce planning bots with different tradeoff preferences, as the bot's perceptions of expected long term rewards are directly linked to plan quality scores.

FIGS. 3 and 4 illustrate flow diagrams of an example RL planning framework for a training phase and a validation/application phase, respectively, in accordance with embodiments of the present disclosure. Particularly, the workflow of the RL training framework is shown in Algorithm 1 and FIGS. 3 and 4. During each iteration n in the training process (see FIG. 3), a random number generator produces a number between 0 and 1, and if the number is larger than the predetermined threshold ε, a random action is taken. Otherwise, optimal policy-based actions indicated by the current Q-function are taken. The introduced randomness in the earlier stages of the training process helps the agent to explore the outcome of performing different actions in different states. is set to 0.05 in this study. This learning approach is known as ε-greedy. The introduced randomness in the earlier stages of the training process can help the agent to possibly explore the outcome of performing different/non-existent actions associated with a state. This learning approach is known as ε-greedy. It allows the planning bot to explore the action-value space and acquire planning knowledge without being fully confined to prior experience. In this study, c is set to gradually decrease over time:

$$\varepsilon = \max(0.05, 1 - E/E_{max}),$$

where E and $E_{max}$ denote current epoch number and maximum epoch number, respectively. The value of c decreases linearly as the number of epochs increases and stays equal or greater to 0.05. It is worth noting that the randomness only exists in the training phase. In the validation phase, the planning bot only follows the guidance of the action-value function in every step.

FIGS. 3 and 4 illustrate flow diagrams of an example RL planning framework for a training phase and a validation/application phase, respectively, in accordance with embodiments of the present disclosure. Particularly, the workflow of the RL training framework is shown in Algorithm 1 and FIGS. 3 and 4. During each iteration n in the training process (see FIG. 3), a random number generator produces a number between 0 and 1, and if the number is larger than the predetermined threshold ε, a random action is taken. Otherwise, optimal policy-based actions indicated by the current Q-function are taken. The introduced randomness in the earlier stages of the training process helps the agent to explore the outcome of performing different actions in different states. is set to 0.05 in this study. This learning approach is known as ε-greedy. The introduced randomness in the earlier stages of the training process can help the agent to possibly explore the outcome of performing different/ non-existent actions associated with a state. This learning approach is known as ε-greedy. It allows the planning bot to explore the action-value space and acquire planning knowledge without being fully confined to prior experience. In this study, ε is set to gradually decrease over time:

$$\varepsilon = \max(0.05, 1 - E/E_{max}),$$

where $E$ and $E_{max}$ denote current epoch number and maximum epoch number, respectively. The value of ε decreases linearly as the number of epochs increases and stays equal or greater to 0.05. It is worth noting that the randomness only exists in the training phase. In the validation phase, the planning bot only follows the guidance of the action-value function in every step.

It allows the learning agent to explore the action-value space and acquire planning knowledge without being fully confined to prior experience based assessment. Note that such randomness is only introduced in the training stage. In the validation phase, the RL agent can follow the guidance of Q-function in every step.

The performance of a system in accordance with embodiments with 40 previously treated biopsy proven pancreatic cancer patients was evaluated. All 40 patients were treated with SIB technique to 25 Gy/33 Gy. The RL system with 14 plans was trained, cycling with 20 epochs, each of which consisted of 15 sequential agent-TPS interactions. For each epoch, the planning agent starts fresh with a pre-set template of optimization constraints. In this example, the only information carried over from an epoch to another is the Q-function. Treatment plans were then generated for remaining 26 patients and compared them with the existing treatment plans.

In order to determine the efficacy of using the proposed RL planning agent in clinical environment, the plan quality was evaluated as set forth herein. The agent behavior was analyzed by analyzing the learning behavior of the planning agent, including state specificity of the agent during the training phase.

With respect to plan quality, all 24 clinical plans and 24 RL plans meet pre-defined GI constraints (V30 Gy<1 cc). The differences between primary PTV coverage of RL plans (98.9%±0.5%) compared to clinical plans (97.6%±0.7%) are significant, while simultaneous integrated boost PTV coverages are similar for clinical plans and RL plans. FIG. 5 depicts images showing dose distributions of three randomly selected validation plans (right column) and their corresponding clinical plans (left column). The RL-plans show similar plan qualities compared to our clinical plans. Referring to FIG. 5, the figure shows axial views of three randomly selected RL validation plans: (right column) and the corresponding clinical plans (left column). The prescription doses to the primary PTV and the boost PTV are 25 Gy and 33 Gy, respectively. 25 Gy and 33 Gy isodose lines are also shown.

With regard to state specificity, FIG. 6 are graphs showing some insight into the RL agent's decision-making process. Referring to FIG. 6, every subplot represents the average feature values when the RL agent decides to take an action. The plots demonstrate that the feature patterns are different across different actions and thus strongly suggest that the RL agent indeed uses meaningful and consistent planning strategies to guide decision-making during planning.

The knowledge map $\theta^T$ contains information regarding the expected plan quality change, measured by the plan quality score function, after a certain action at a certain state. An action is usually considered optimal when the state value is well aligned with the knowledge map $\theta^T$. This characteristic of the model makes the model interpretable. For example, FIGS. 7 and 8 show two regions of the reshaped $\theta^T$. Particularly, the weighting vector $\theta^T$ re-shaped based on features and actions. At each agent-TPS interaction, action-value $Q(s,a)$ is obtained by multiplying $\theta T$ by the feature vector $\varphi(s,a)$, which is evaluated in the TPS at the step.

FIG. 7 illustrates that the agent has learned that when both $PTV_{33\ Gy}$ coverage and stomach 1 cc constraints are compromised, it should consider adding lower constraint to an auxiliary structure that avoids the overlapping region between the PTV and the stomach. In contrast, it is often not effective to directly add PTV lower constraints. Similarly, FIG. 8 shows that adding stomach+6 mm upper constraints may be preferred when PTV33 Gy D98 is slightly violated and the stomach D1 cc dose constraint is violated. Such learned knowledge suggests that the RL agent learns to make sensible choices given the state information and our formulation of the action-value function offers meaningful insights into the learned planning strategies in the form of a knowledge map. The RL learning provides a systematic and subjective methodology of learning planning strategies and related knowledge.

Experiments have also demonstrated that the training of the RL agent is highly reproducible. FIGS. 9 and 10 are graphs that show the average knowledge map differences in two different training sessions. Particularly, FIGS. 9 and 10 show average knowledge map differences across different features and different actions, respectively. The average absolute change is 2.5%. Considering the fact that the training sessions heavily involve introduced stochasticity, the differences between the two knowledge maps are relatively small, which demonstrates that the model training procedure is robust and reproducible.

In pancreas SBRT treatment planning, GI structures (bowel, c-loop, and stomach) are often the limiting factors of boost PTV coverage. Planners have to evaluate the plan with respect to the GI constraints and make adjustments accordingly. Notably, a few actions are often taken when a planner modifies a plan. These actions include adjusting priority or placement of existing structures and added auxiliary structures. This process is formalized into a finite-horizon reinforcement-learning framework, the crucial components of which include states, actions, and rewards. First, systems and methods disclosed herein have discretized states, in a similar fashion to how planners evaluate plans (i.e. constraint satisfaction). Second, a set of common actions that planners have been identified that can take to address different planning issues, such as coverage, dose spill, etc. Third, we have derived a reward system based on our physician's input. Finally, the dimensionality of the systems have been limited.

The training process of the Q-learning algorithm essentially simulates the training of a human planner. The agent may take many attempts in trying different actions at different states, and after each action, the plan is re-evaluated, and a reward is assigned accordingly. After the training process, the agent can learn to interact with the environment to get the highest reward possible. The knowledge is summarized in a Q-function, which contains the information of expected long-term rewards of taking certain actions at certain states. During treatment planning, the agent periodically evaluates the current state of the plan, infers the best option from the Q-function, and takes the corresponding action.

Table 2 below lists example elements of a state vector $f(s)$ that may be used in a planning bot. These values were set based on set clinical constraints.

TABLE 2

State vector f(s) for a RL planning program.

| Index | Structure | Intermediate dose D | Expected dose D |
|---|---|---|---|
| 1 | $PTV_{pri}$ | $D_{95\%}$ | 25 Gy |
| 2 | $PTV_{bst}$ | $D_{95\%}$ | 33 Gy |
| 3 | $PTV_{bst}$ minus (Bowel expanded by 3 mm) minus (Duodenum expanded by 3 mm) minus (Stomach expanded by 3 mm) | $D_{95\%}$ | 33 Gy |
| 4 | Bowel | $D_{1\,cc}$ | 30 Gy |
| 5 | Duodenum | $D_{1\,cc}$ | 30 Gy |
| 6 | Stomach | $D_{1\,cc}$ | 30 Gy |
| 7 | Liver | $D_{50\%}$ | 12 Gy |
| 8 | Kidneys | $D_{25\%}$ | 12 Gy |
| 9 | Cord | $D_{max}$ | 20 Gy |
| 10 | $PTV_{pri} - (PTV_{bst}$ expanded by 3 mm) | $D_{10\%}$ | 30 Gy |

FIG. 11 shows a full weighting vector learned by the planning bot after a training session. The weighting factor can be later used to guide the planning bot to make planning decisions. The weighting vector $\theta^T$ can be re-shaped based on features and actions. At each bot-TPS interaction, action-value Q(s,a) can be obtained by multiplying $\theta^T$ by the feature vector φ(s,a), which is evaluated in the TPS at the step.

The present subject matter may be a system, a method, and/or a computer program product. The computer program product may include a computer readable storage medium (or media) having computer readable program instructions thereon for causing a processor to carry out aspects of the present subject matter.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a RAM, a ROM, an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network, or Near Field Communication. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present subject matter may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java, Smalltalk, C++, Javascript or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present subject matter.

Aspects of the present subject matter are described herein with reference to flowchart illustrations and/or block diagrams of methods, apparatus (systems), and computer program products according to embodiments of the subject matter. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present subject matter. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

While the embodiments have been described in connection with the various embodiments of the various figures, it is to be understood that other similar embodiments may be used, or modifications and additions may be made to the described embodiment for performing the same function without deviating therefrom. Therefore, the disclosed embodiments should not be limited to any single embodiment, but rather should be construed in breadth and scope in accordance with the appended claims.

What is claimed is:

1. A method comprising:
at least one computing device:
receiving anatomical and/or geometric characterization data of at least one target volume for radiation treatment of a patient;
receiving anatomical and/or geometric characterization data of at least one organ at risk (OAR) proximate the target volume;
constructing a treatment planning strategies model for applying a predetermined radiation dosage to the target volume based on the received data, wherein the model comprises planning states and associated planning actions selectable to implement at each state, wherein each planning action is associated with a reward based on radiation treatment knowledge, the state and the data, and wherein the model is constrained by a predetermined limit of radiation dosage to the at least one organ at risk;
presenting information about at least one planning state and the planning actions associated with the at least one planning state;
receiving the rewards associated with the planning actions associated with the at least one planning state;
receiving selection of a planning action associated with the at least one planning state;
receiving selection of a next planning state associated with the selected planning action;
receiving quality value information associated with the selected planning action, the selected next planning state, and planning actions associated with the selected next planning state; and
reconstructing the model based on the received selection of the planning action and the quality value information.

2. The method of claim 1, wherein constructing the model comprises constructing the model based on one or more of patient image, patient organ contour information, target volume contour information, and clinical parameters.

3. The method of claim 1, wherein constructing the model comprises constructing the model based on geometric characterization of a plurality of distances from the target volume.

4. The method of claim 1, wherein the geometric characterization data of the target volume comprises one of a size and shape of the target volume.

5. The method of claim 1, wherein the geometric characterization data of the at least one organ at risk comprises one of a size and shape of the at least one organ at risk.

6. The method of claim 1, wherein constructing the treatment planning strategies model comprises constructing the treatment planning strategies model based on radiation treatment knowledge data, wherein the radiation treatment knowledge data comprises information about one of radiation treatment knowledge, experience, and preferences, and computerized models of published clinical trials results and guidelines for radiation treatment.

7. The method of claim 1, wherein the model is based on parameters represented by at least one of a dose distribution and the dose volume histogram.

8. The method of claim 1, wherein each planning state is a representation of a current status of the planning process which includes characterization of current optimization parameters and a current plan including at least one of measurements of the plan's conformity to dose constraints on target, OARs, and other auxiliary structures.

9. The method of claim 1, wherein each planning action includes at least one of increasing or decreasing dose constraints to the target, OARs, or other auxiliary structures.

10. The method of claim 1, wherein the reward is calculated based on a plan quality score comprising weighted sum of multiple estimates of plan quality measurements which include both hard and soft constraints on dose-volume values.

11. The method of claim 1, wherein reconstructing the model comprises adjusting the quality value information associated with planning states and associated planning actions based on rewards and associated quality value information of the received selection of the planning action.

12. The method of claim 11, wherein the quality value information is based on a sequence of planning actions selected for a sequence of next planning states.

13. The method of claim 11, wherein applying a predetermined radiation dosage to the at least one target volume and constraining to a predetermined limit of radiation dosage to the at least one organ at risk comprise utilization of and interaction with a treatment planning system involving optimization algorithms and dose calculation algorithms.

14. The method of claim 11, further comprising presenting information about the reconstructed model.

15. A system comprising:
a radiation therapy planner configured to:
receive anatomical and/or geometric characterization data of at least one target volume for radiation treatment of a patient;
receive anatomical and/or geometric characterization data of at least one organ at risk (OAR) proximate the target volume;
construct a treatment planning strategies model for applying a predetermined radiation dosage to the target volume based on the received data, wherein the model comprises planning states and associated planning actions selectable to implement at each state, wherein each planning action is associated with a reward based on radiation treatment knowledge, the state and the data, and wherein the model is constrained by a predetermined limit of radiation dosage to the at least one organ at risk;

present information about at least one planning state and the planning actions associated with the at least one planning state;

receive the rewards associated with the planning actions associated with the at least one planning state;

receive selection of a planning action associated with the at least one planning state;

receive selection of a next planning state associated with the selected planning action;

receive a quality value information associated with the selected planning action, the selected next planning state, and planning actions associated with the selected next planning state; and reconstruct the model based on the received selection of the planning action and the quality value information.

16. The system of claim 15, wherein the radiation therapy planner is configured to construct the model based on one or more of patient image, patient organ contour information, target volume contour information, and clinical parameters.

17. The system of claim 15, wherein the geometric characterization data of the target volume comprises one of a size and shape of the target volume.

18. The system of claim 15, wherein the treatment planning strategies model are constructed based on radiation treatment knowledge data, wherein the radiation treatment knowledge data comprises information about one of radiation treatment knowledge, experience, and preferences, and computerized models of published clinical trials results and guidelines for radiation treatment.

19. The system of claim 15, wherein each planning state is a representation of a current status of the planning process which includes characterization of a current optimization parameters and a current plan including at least one of measurements of the plan's conformity to dose constraints on target, OARs, and other auxiliary structures.

20. The system of claim 15, wherein each planning action includes at least one of increasing or decreasing constraints to the target, OARs, or other auxiliary structures.

21. The system of claim 15, wherein the radiation therapy planner is configured to adjust the quality value information associated with planning states and associated planning actions based on rewards and associated quality value information of the received selection of the planning action.

22. A method comprising:
receiving radiation treatment knowledge and planning strategies data;
providing a planning strategies model for applying a predetermined radiation dosage to a target volume and constrained by a predetermined limit of radiation dosage to at least one organ at risk, wherein the model explicitly represents planning strategies comprising planning states and associated planning actions, wherein each planning state is associated with one or more planning actions that are determined to be most appropriate for the planning state, each planning action being constructed based on the radiation treatment knowledge and planning strategies data;

receiving information about a current state of a subject; and applying the planning strategies in the model repeatedly to generate a sequence of planning states and planning actions until a final planning state is reached, wherein the final planning state meets the predetermined radiation dosage to the target volume and the predetermined limit of radiation dosage to the at least one organ at risk.

23. The method of claim 22, further comprising constructing the planning strategies model by:
receiving anatomical and/or geometric characterization data of at least one target volume for radiation treatment of a patient;
receiving anatomical and/or geometric characterization data of at least one organ at risk proximate the target volume;
constructing a treatment planning strategies model for applying a predetermined radiation dosage to the target volume based on the received data, wherein the model comprises planning states and associated planning actions selectable to implement at each state, wherein each planning action is associated with a reward based on radiation treatment knowledge, the state and the data, and wherein the model is constrained by a predetermined limit of radiation dosage to the at least one organ at risk;
presenting information about at least one planning state and the planning actions associated with the at least one planning state;
receiving the rewards associated with the planning actions associated with the at least one planning state;
receiving selection of a planning action associated with the at least one planning state;
receiving selection of a next planning state associated with the selected planning action;
receiving quality value information associated with the selected planning action, the selected next planning state, and planning actions associated with the selected next planning state; and
reconstructing the model based on the received selection of the planning action and the quality value information.

24. The method of claim 22, further comprising receiving user input indicating each planning action.

25. The method of claim 24, wherein the user input comprises acquired decisions of one or more healthcare planners.

26. The method of claim 24, wherein the planning actions are selectable to implement at each state, and wherein each planning action is associated with a reward based on the radiation treatment knowledge and the data.

27. The method of claim 22, further comprising generating another model and one or more planning states based on a treatment planning system or an optimization algorithm.

* * * * *